(12) United States Patent
Joseph

(10) Patent No.: US 10,966,856 B2
(45) Date of Patent: *Apr. 6, 2021

(54) FOAM CORE SANDWICH SPLINT

(71) Applicant: DJO, LLC, Vista, CA (US)

(72) Inventor: Mark Joseph, Aspen, CO (US)

(73) Assignee: DJO, LLC, Vista, CA (US)

( * ) Notice: Subject to any disclaimer, the term of this patent is extended or adjusted under 35 U.S.C. 154(b) by 76 days.

This patent is subject to a terminal disclaimer.

(21) Appl. No.: 16/405,196

(22) Filed: May 7, 2019

(65) Prior Publication Data

US 2019/0254861 A1    Aug. 22, 2019

Related U.S. Application Data

(63) Continuation of application No. 15/082,690, filed on Mar. 28, 2016, now Pat. No. 10,285,845, which is a
(Continued)

(51) Int. Cl.
*A61F 5/00*    (2006.01)
*A61F 5/058*    (2006.01)
(Continued)

(52) U.S. Cl.
CPC ............ *A61F 5/05825* (2013.01); *A61F 5/01* (2013.01); *A61F 5/0102* (2013.01); *A61L 15/12* (2013.01);
(Continued)

(58) Field of Classification Search
CPC ...... A61F 5/01; A61F 5/0102; A61F 5/05825; A61F 13/04; B32B 2535/00
See application file for complete search history.

(56) References Cited

U.S. PATENT DOCUMENTS

| 57,283 A | 8/1866 | Brown |
|---|---|---|
| D19,360 S | 10/1889 | Sanders |

(Continued)

FOREIGN PATENT DOCUMENTS

| CN | 2902232 | 5/2007 |
|---|---|---|
| CN | 101279110 | 10/2008 |

(Continued)

OTHER PUBLICATIONS

Aquaplast Splinting Materials, http://www.wisdomking.com/aquaplast-splinting, archived 2008.
(Continued)

*Primary Examiner* — Kim M Lewis
(74) *Attorney, Agent, or Firm* — Knobbe, Martens, Olson & Bear LLP

(57) ABSTRACT

A multi-layered composite material suitable for use in orthopedics includes a foam core layer bonded between two layers of thermoformable polymer material. The thermoformable material is heat formable within a target temperature range allowing for rapid heating and application to a patient such as in the form of a splint. While within the target temperature range, the composite material includes a dwell time sufficiently long to enable proper fitment and adjustment, yet not overly long requiring extended periods of holding the composite material in place. The composite material is very light yet extremely rigid and easily conformable to patients.

20 Claims, 2 Drawing Sheets

Related U.S. Application Data continuation of application No. 13/836,660, filed on Mar. 15, 2013, now Pat. No. 9,295,748.

(60) Provisional application No. 61/677,779, filed on Jul. 31, 2012.

(51) Int. Cl.
*A61L 15/14* (2006.01)
*A61F 5/01* (2006.01)
*A61L 15/12* (2006.01)
*B32B 5/18* (2006.01)

(52) U.S. Cl.
CPC ............... *A61L 15/14* (2013.01); *B32B 5/18* (2013.01); *B32B 2309/02* (2013.01); *B32B 2535/00* (2013.01)

(56) References Cited

U.S. PATENT DOCUMENTS

| | | |
|---|---|---|
| 482,647 A | 9/1892 | Obear |
| D35,545 S | 12/1901 | Schaefer |
| 911,243 A | 2/1909 | Johannesen |
| 975,734 A | 11/1910 | Tebeau |
| 1,082,542 A | 12/1913 | Manson |
| 1,360,840 A | 11/1920 | White |
| 1,477,070 A | 3/1922 | Martin |
| 1,471,948 A | 10/1923 | Cox et al. |
| 1,583,606 A | 5/1926 | Roussel |
| 2,070,810 A | 2/1937 | Saling |
| 2,181,689 A | 11/1939 | Bell |
| 2,206,404 A | 7/1940 | Jones |
| 2,477,040 A | 3/1945 | Brown et al. |
| 2,554,337 A | 5/1951 | Lampert |
| 2,736,314 A | 2/1956 | Hale |
| 2,759,475 A | 8/1956 | Swaay |
| 2,818,063 A | 12/1957 | Smith et al. |
| 2,904,040 A | 9/1959 | Hale |
| D198,069 S | 4/1964 | Connelly |
| D203,018 S | 11/1965 | Helferich |
| 3,230,952 A | 1/1966 | Reyes Terron |
| 3,302,642 A | 2/1967 | Allen |
| 3,306,284 A | 2/1967 | McKinley |
| 3,313,297 A | 4/1967 | Applegate et al. |
| 3,320,950 A | 5/1967 | McElvenny |
| 3,420,231 A | 1/1969 | Edenbaum |
| 3,490,444 A | 1/1970 | Larson |
| 3,512,523 A | 5/1970 | Barnett |
| 3,692,023 A | 9/1972 | Phillips et al. |
| 3,788,307 A | 1/1974 | Kistner |
| 3,896,843 A | 7/1975 | Millar et al. |
| 3,906,943 A | 9/1975 | Arluck |
| 3,916,885 A | 11/1975 | Gaylord, Jr. |
| 3,924,272 A | 12/1975 | Allen et al. |
| 4,006,741 A | 2/1977 | Arluck |
| 4,019,505 A | 4/1977 | Wartman |
| 4,136,686 A | 1/1979 | Arluck |
| 4,169,469 A | 10/1979 | Arluck |
| 4,193,395 A | 3/1980 | Gruber |
| D256,055 S | 7/1980 | Finnieston |
| 4,235,228 A | 11/1980 | Gaylord et al. |
| 4,240,415 A | 12/1980 | Wartman |
| D259,955 S | 7/1981 | Helferich |
| 4,286,586 A | 9/1981 | Potts |
| 4,316,457 A | 2/1982 | Liegeois |
| D266,288 S | 9/1982 | Coon |
| 4,379,463 A | 4/1983 | Meier et al. |
| D270,284 S | 8/1983 | Lindh et al. |
| 4,427,002 A | 1/1984 | Baron et al. |
| 4,441,711 A | 4/1984 | Dubar et al. |
| 4,442,834 A | 4/1984 | Tucker et al. |
| 4,454,873 A | 6/1984 | Laufenberg et al. |
| 4,471,993 A | 9/1984 | Watson |
| 4,473,671 A | 9/1984 | Green |
| 4,482,414 A | 11/1984 | Schonberger |
| 4,483,333 A | 11/1984 | Wartman |
| 4,510,927 A | 4/1985 | Peters |
| 4,531,241 A | 7/1985 | Berger |
| 4,572,167 A | 2/1986 | Brunswick |
| 4,584,993 A | 4/1986 | Nelson |
| 4,600,618 A | 7/1986 | Raychok, Jr. et al. |
| D287,640 S | 1/1987 | Primiano |
| 4,661,535 A | 4/1987 | Borroff |
| 4,726,361 A | 2/1988 | Farley |
| 4,765,319 A | 8/1988 | Finnieston et al. |
| 4,770,299 A | 9/1988 | Parker |
| 4,784,123 A | 11/1988 | Robeson |
| 4,827,915 A | 5/1989 | Gorsen |
| 4,872,448 A | 10/1989 | Johnson |
| 4,888,225 A | 12/1989 | Sandvig et al. |
| 4,912,174 A | 3/1990 | Grouiller |
| 4,946,726 A | 8/1990 | Sandvig et al. |
| 4,955,368 A | 9/1990 | Heimann |
| 5,031,607 A | 7/1991 | Peters |
| 5,038,759 A | 8/1991 | Morgenstern |
| 5,058,576 A | 10/1991 | Grim et al. |
| 5,098,778 A | 3/1992 | Minnick |
| D326,719 S | 6/1992 | Eghamn |
| 5,151,315 A | 9/1992 | Ponnet |
| 5,158,098 A | 10/1992 | Jalalian |
| 5,180,361 A | 1/1993 | Moore et al. |
| 5,230,698 A | 7/1993 | Garth |
| 5,316,604 A | 5/1994 | Fell |
| RE34,714 E | 8/1994 | Burns et al. |
| 5,364,693 A | 11/1994 | Moren et al. |
| 5,366,439 A | 11/1994 | Peters |
| D357,745 S | 4/1995 | Radwell |
| 5,409,761 A | 4/1995 | Langley |
| 5,415,622 A | 5/1995 | Kelley |
| D363,780 S | 10/1995 | Darby et al. |
| 5,454,780 A | 10/1995 | Duback et al. |
| 5,520,529 A | 5/1996 | Heckel |
| D373,639 S | 9/1996 | McKie |
| 5,554,104 A | 9/1996 | Grim |
| 5,599,288 A | 2/1997 | Shirley et al. |
| 5,624,386 A | 4/1997 | Tailor et al. |
| 5,632,722 A | 5/1997 | Tweardy et al. |
| 5,688,229 A | 11/1997 | Bauer |
| 5,737,774 A | 4/1998 | Petty-Saphon et al. |
| 5,752,873 A | 5/1998 | Morris |
| 5,752,926 A | 5/1998 | Larson et al. |
| D395,514 S | 6/1998 | Stano |
| 5,763,047 A | 6/1998 | Green |
| 5,769,804 A | 6/1998 | Harris et al. |
| 5,807,291 A | 9/1998 | Larson et al. |
| 5,819,312 A | 10/1998 | Snyder et al. |
| 5,823,984 A | 10/1998 | Silverberg |
| 5,826,304 A | 10/1998 | Carlson |
| 5,830,167 A | 11/1998 | Jung |
| D405,180 S | 2/1999 | Reina |
| 5,865,778 A | 2/1999 | Johnson |
| 5,882,322 A | 3/1999 | Kim et al. |
| 5,902,259 A | 5/1999 | Wilkerson |
| 5,926,843 A | 7/1999 | Winchester |
| 5,934,599 A | 8/1999 | Hammerslag |
| 5,951,504 A | 9/1999 | Iglesias et al. |
| 5,971,946 A | 10/1999 | Quinn et al. |
| 5,982,285 A | 11/1999 | Bueche et al. |
| 6,042,557 A | 3/2000 | Ferguson et al. |
| 6,053,884 A | 4/2000 | Peters |
| 6,056,671 A | 5/2000 | Marmer |
| 6,056,713 A | 5/2000 | Hayashi |
| RE36,745 E | 6/2000 | Rudy, Jr. et al. |
| 6,093,161 A | 7/2000 | Vlaeyen et al. |
| 6,110,134 A | 8/2000 | Clark, Jr. et al. |
| 6,146,240 A | 11/2000 | Morris |
| D436,177 S | 1/2001 | Miller |
| 6,168,966 B1 | 1/2001 | Grim et al. |
| 6,179,798 B1 | 1/2001 | Nelson |
| D437,416 S | 2/2001 | Slautterback |
| 6,186,966 B1 | 2/2001 | Grim et al. |
| 6,202,953 B1 | 3/2001 | Hammerslag |
| 6,254,560 B1 | 7/2001 | Tweardy et al. |

(56) References Cited

U.S. PATENT DOCUMENTS

| | | |
|---|---|---|
| 6,289,558 B1 | 9/2001 | Hammerslag |
| 6,322,529 B1 | 11/2001 | Chung |
| 6,325,772 B1 | 12/2001 | Scheuermann et al. |
| 6,358,220 B1 | 3/2002 | Langen et al. |
| 6,393,810 B1 | 5/2002 | Mier |
| 6,416,074 B1 | 7/2002 | Maravets et al. |
| 6,423,020 B1 | 7/2002 | Koledin |
| D463,565 S | 9/2002 | Slautterback |
| 6,470,832 B1 | 10/2002 | Peacock |
| 6,509,078 B1 | 1/2003 | Beckmann |
| 6,520,925 B1 | 2/2003 | Thibodo, Jr. |
| D473,653 S | 4/2003 | Weaver, II et al. |
| D477,088 S | 7/2003 | Brown et al. |
| D477,409 S | 7/2003 | Mills et al. |
| D477,410 S | 7/2003 | Wiggins et al. |
| 6,602,215 B1 | 8/2003 | Richie, Jr. |
| 6,663,581 B1 | 12/2003 | Calabrese |
| D492,787 S | 7/2004 | Weaver, II et al. |
| 6,779,282 B2 | 8/2004 | Grohninger |
| D496,465 S | 9/2004 | Weaver, II |
| D500,855 S | 1/2005 | Pick et al. |
| 6,843,190 B1 | 1/2005 | LaPierre-McAfee |
| 6,872,188 B2 | 3/2005 | Caille et al. |
| D505,727 S | 5/2005 | Krahner et al. |
| 6,893,410 B1 | 5/2005 | Hely |
| 6,922,917 B2 | 8/2005 | Kerns et al. |
| 6,960,176 B1 | 11/2005 | Hely et al. |
| 7,001,348 B2 | 2/2006 | Garth et al. |
| D518,895 S | 4/2006 | Weaver, II et al. |
| D519,211 S | 4/2006 | Doty et al. |
| 7,025,737 B2 | 4/2006 | Modglin |
| 7,041,073 B1 | 5/2006 | Patron |
| 7,056,298 B1 | 6/2006 | Weber |
| 7,082,701 B2 | 8/2006 | Dalgaard et al. |
| 7,083,585 B2 | 8/2006 | Latham |
| 7,090,653 B2 | 8/2006 | Moeller |
| D530,016 S | 10/2006 | Sroufe et al. |
| 7,141,031 B2 | 11/2006 | Garth et al. |
| 7,182,741 B2 | 2/2007 | Porrata et al. |
| 7,204,817 B1 | 4/2007 | Toronto et al. |
| D542,919 S | 5/2007 | Leatt |
| 7,217,060 B2 | 5/2007 | Ingimarsson |
| D550,370 S | 9/2007 | Peters et al. |
| D552,743 S | 10/2007 | Verkade et al. |
| D552,744 S | 10/2007 | Verkade et al. |
| D558,883 S | 1/2008 | Ortiz |
| 7,316,660 B1 | 1/2008 | Modglin |
| 7,329,229 B2 | 2/2008 | Scheinberg et al. |
| D565,189 S | 3/2008 | Gramza et al. |
| 7,392,602 B2 | 7/2008 | Reagan et al. |
| 7,399,288 B2 | 7/2008 | Chao |
| D580,064 S | 11/2008 | Lin et al. |
| D580,555 S | 11/2008 | Lin et al. |
| 7,449,006 B2 | 11/2008 | Wolanske |
| 7,470,243 B2 | 12/2008 | Garth |
| D584,822 S | 1/2009 | Weber |
| 7,507,215 B2 | 3/2009 | Ryan |
| 7,591,050 B2 | 9/2009 | Hammerslag |
| 7,597,671 B2 | 10/2009 | Baumgartner et al. |
| 7,608,052 B1 | 10/2009 | Baker |
| 7,645,250 B2 | 1/2010 | Koby et al. |
| 7,674,234 B2 | 3/2010 | Calco et al. |
| D616,556 S | 5/2010 | Hu |
| D617,464 S | 6/2010 | Weaver, II et al. |
| 7,727,172 B2 | 6/2010 | Wang |
| D626,242 S | 10/2010 | Sagnip et al. |
| D626,244 S | 10/2010 | Sagnip et al. |
| D628,300 S | 11/2010 | Caden |
| D628,696 S | 12/2010 | Robertson |
| D629,115 S | 12/2010 | Robertson |
| 7,846,118 B2 | 12/2010 | Sandhu |
| 7,854,714 B1 | 12/2010 | Weber et al. |
| 7,874,997 B2 | 1/2011 | Jaccard |
| D632,401 S | 2/2011 | Stevens |
| 7,883,485 B2 | 2/2011 | Moenning et al. |
| D633,622 S | 3/2011 | Chiang |
| D633,623 S | 3/2011 | Leatt et al. |
| D635,269 S | 3/2011 | Franke et al. |
| D635,270 S | 3/2011 | Chiang |
| D635,682 S | 4/2011 | Chiang |
| D636,494 S | 4/2011 | Garth et al. |
| D638,948 S | 5/2011 | Janzon |
| 7,942,837 B2 | 5/2011 | Clark et al. |
| 7,950,112 B2 | 5/2011 | Hammerslag et al. |
| D639,965 S | 6/2011 | Wehsely-Swiczinsky |
| 7,954,204 B2 | 6/2011 | Hammerslag et al. |
| 7,955,287 B2 | 6/2011 | Frangi |
| D641,482 S | 7/2011 | Robertson et al. |
| D641,483 S | 7/2011 | Robertson et al. |
| D643,978 S | 8/2011 | Abajo Alonso et al. |
| 7,992,261 B2 | 8/2011 | Hammerslag et al. |
| D647,623 S | 10/2011 | Thorgilsdottir et al. |
| D647,624 S | 10/2011 | Thorgilsdottir et al. |
| D649,648 S | 11/2011 | Cavalieri et al. |
| D649,649 S | 11/2011 | Leatt et al. |
| D649,650 S | 11/2011 | Wehsely-Swiczinsky |
| 8,057,417 B2 | 11/2011 | Imai |
| D650,485 S | 12/2011 | Jaccard |
| D652,937 S | 1/2012 | Robertson et al. |
| 8,091,182 B2 | 1/2012 | Hammerslag et al. |
| D654,180 S | 2/2012 | Weaver, II |
| D657,062 S | 4/2012 | Chiang |
| D657,063 S | 4/2012 | Chiang |
| D663,850 S | 7/2012 | Joseph |
| D663,851 S | 7/2012 | Joseph |
| D663,852 S | 7/2012 | Joseph |
| D664,259 S | 7/2012 | Joseph |
| D665,088 S | 8/2012 | Joseph |
| D666,301 S | 8/2012 | Joseph |
| D666,302 S | 8/2012 | Joseph |
| 8,246,560 B2 | 8/2012 | Gaylord et al. |
| 8,277,401 B2 | 10/2012 | Hammerslag et al. |
| 8,303,527 B2 | 11/2012 | Joseph |
| D687,556 S | 8/2013 | Joseph |
| 8,856,972 B2 | 10/2014 | Kirshon |
| 8,951,217 B2 | 2/2015 | Joseph |
| 9,295,748 B2 * | 3/2016 | Joseph .................. A61F 5/0102 |
| 9,408,738 B2 | 8/2016 | Boraas et al. |
| 9,561,128 B2 | 2/2017 | Joseph |
| 9,655,761 B2 | 5/2017 | Joseph et al. |
| 9,757,265 B2 | 9/2017 | Joseph |
| 10,285,845 B2 * | 5/2019 | Joseph ................ A61F 5/05825 |
| 2002/0068890 A1 | 6/2002 | Schwenn et al. |
| 2002/0095750 A1 | 7/2002 | Hammerslag |
| 2002/0148461 A1 | 10/2002 | Heinz et al. |
| 2002/0161114 A1 | 10/2002 | Gunatillake et al. |
| 2003/0178404 A1 | 9/2003 | Dimartino et al. |
| 2003/0204938 A1 | 11/2003 | Hammerslag |
| 2004/0024337 A1 | 2/2004 | Tseng et al. |
| 2004/0034316 A1 | 2/2004 | Castro |
| 2004/0255955 A1 | 12/2004 | Daly |
| 2005/0033207 A1 | 2/2005 | Anders |
| 2005/0034686 A1 | 2/2005 | Spatt |
| 2005/0043664 A1 | 2/2005 | Reaux |
| 2005/0101898 A1 | 5/2005 | Cohen |
| 2005/0197606 A1 | 9/2005 | Preire |
| 2005/0251074 A1 | 11/2005 | Latham |
| 2005/0273030 A1 | 12/2005 | Koby et al. |
| 2005/0281999 A1 | 12/2005 | Hofmann et al. |
| 2006/0051402 A1 | 3/2006 | Bogardus et al. |
| 2006/0052730 A1 | 3/2006 | Hargrave et al. |
| 2006/0062991 A1 | 3/2006 | Sendijarevic et al. |
| 2006/0129075 A1 | 6/2006 | Scheinberg et al. |
| 2006/0155226 A1 | 7/2006 | Grim et al. |
| 2006/0156517 A1 | 7/2006 | Hammerslag et al. |
| 2006/0173390 A1 | 8/2006 | Van Wyk et al. |
| 2007/0004993 A1 | 1/2007 | Coppens et al. |
| 2007/0077393 A1 | 4/2007 | Chiang et al. |
| 2007/0179417 A1 | 8/2007 | Schwenn et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |

(56) References Cited

U.S. PATENT DOCUMENTS

| | | |
|---|---|---|
| 2008/0082033 A1 | 4/2008 | Ortiz |
| 2008/0083135 A1 | 4/2008 | Hammerslag et al. |
| 2008/0177210 A1 | 7/2008 | McDevitt Larson |
| 2008/0262400 A1 | 10/2008 | Clark et al. |
| 2009/0082707 A1 | 3/2009 | Rumsey |
| 2009/0192425 A1 | 7/2009 | Garth et al. |
| 2009/0192427 A1 | 7/2009 | Brown et al. |
| 2009/0204042 A1 | 8/2009 | Park |
| 2009/0204047 A1 | 8/2009 | MacArthur |
| 2009/0264802 A1 | 10/2009 | Chen |
| 2010/0168630 A1 | 7/2010 | Cropper et al. |
| 2010/0185130 A1 | 7/2010 | Rizo Patron |
| 2010/0262054 A1 | 10/2010 | Summit et al. |
| 2010/0268139 A1 | 10/2010 | Garth |
| 2010/0268140 A1 | 10/2010 | Berlese |
| 2010/0268141 A1 | 10/2010 | Bannister |
| 2010/0299959 A1 | 12/2010 | Hammerslag et al. |
| 2010/0318010 A1 | 12/2010 | Sandifer et al. |
| 2011/0034844 A1 | 2/2011 | Thorgilsdottir et al. |
| 2011/0082402 A1 | 4/2011 | Oddou et al. |
| 2011/0130694 A1 | 6/2011 | Livolsi et al. |
| 2011/0213284 A1 | 9/2011 | Garth et al. |
| 2011/0313389 A1 | 12/2011 | Wood et al. |
| 2012/0065562 A1 | 3/2012 | Kaphingst |
| 2012/0101417 A1* | 4/2012 | Joseph ............... A61F 5/05841 602/5 |
| 2013/0260080 A1 | 10/2013 | Roberts |
| 2013/0274744 A1 | 10/2013 | Ikemizu |
| 2013/0338554 A1 | 12/2013 | Pflaster |
| 2015/0119775 A1 | 4/2015 | Gildersleeve et al. |
| 2017/0014216 A1 | 1/2017 | Boraas et al. |
| 2017/0089241 A1 | 7/2017 | Joseph |
| 2017/0349135 A1 | 12/2017 | Joseph |
| 2018/0055671 A1 | 3/2018 | Joseph |
| 2020/0237547 A1 | 7/2020 | Joseph |

FOREIGN PATENT DOCUMENTS

| | | |
|---|---|---|
| CN | 201798833 U | 4/2011 |
| CN | 201996695 U | 10/2011 |
| CN | 102333502 | 1/2012 |
| EP | 0 393 003 | 10/1990 |
| EP | 0 401 883 | 12/1990 |
| EP | 0 619 102 | 10/1994 |
| EP | 0 625 342 | 11/1994 |
| EP | 0 795 307 | 4/2004 |
| JP | 09-234241 | 9/1997 |
| JP | 2004-065912 | 3/2004 |
| WO | WO 93/21967 | 11/1993 |
| WO | WO 07/035875 | 3/2007 |
| WO | WO 10/099130 | 9/2010 |
| WO | WO 11/071264 | 6/2011 |
| WO | WO 12/098424 | 7/2012 |
| WO | WO 12/138523 | 10/2012 |

OTHER PUBLICATIONS

Johnson & Johnson Orthoplast Splinting Materials, http://www.medco-school.com/Supply/Product.asp?Leaf_ld-80365, archived 2007.

* cited by examiner

| PROPERTIES | TEST METHOD | |
|---|---|---|
| Hardness | ASTM D2240 | 76D |
| Thickness | | 0.030" - 0.075" |
| Specific Gravity | ASTM D792 | 1.20 g/cm$^3$ |
| Tensile Strength | ASTM D638 | 7500 psi |
| Elongation @ Brk | ASTM D638 | 5% |
| Flexural Modulus | ASTM D5023 | 308,000 psi |

| PROPERTY | TEST PROCEDURE | UNITS | |
|---|---|---|---|
| Nominal Density - Skin/Skin | BS ISO 7214 2007 | kg/m³ | 300 |
| Nominal Thickness | BS EN ISO 1923 | mm | 1 |
| Compression Stress-Strain | BS ISO 7214 2007 | | |
| 25% compression | | kPa | 180 |
| 50% compression | | kPa | 795 |
| Compression Set | BS ISO 7214 2007 25mm cell-cell | | |
| 25% comp., 22hr, 23°C 1/2 hour recovery | | % set | 13.5 |
| 24hr recovery | | % set | 6 |
| machine direction | ISO 7214 2007 | kPa | |
| Tensile Strength | | % | 3600 |
| Tensile Elongation | | | 138 |
| crossweb | ISO 7214 2007 | kPa | |
| Tensile Strength | | % | 3025 |
| Tensile Elongation | | | 145 |
| Shore Hardness A Scale 10mm stacked | ISO 868 1985 | A | 52 |

Figure 3

FOAM CORE SANDWICH SPLINT

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/082,690, filed Mar. 28, 2016, now U.S. Pat. No. 10,285,845, which is a continuation of U.S. application Ser. No. 13/836,660, filed Mar. 15, 2013, now U.S. Pat. No. 9,295,748, which claims the benefit of U.S. Provisional Application No. 61/677,779, filed Jul. 31, 2012. Each of the aforementioned applications is incorporated by reference herein in its entirety, and each is hereby expressly made a part of this specification.

FIELD OF THE INVENTION

The present invention related generally to orthopedic braces. More specifically, the present invention relates to a thermoformable splint having a composite material construction.

BACKGROUND OF THE INVENTION

Orthopedic splints are typically used during the first few days of a serious injury such as a fracture, ligament tear or other injury that needs to be stabilized while swelling subsides. Splints are typically partially circumferential or they may wrap around an elbow or ankle and extend up both sides allowing a space on either side. They allow for swelling to occur and are typically wrapped with an Ace®-type bandage or the like, which is elastic and may provide compression, yet stretches to accommodate swelling. A complication, Compartment Syndrome, may occur if an injury is casted too soon or splinted too tightly which causes tissue to rapidly die from pressure buildup. Temporary proper splinting mitigates most complications in this regard. Typically, after 4-10 days, the splint is removed for procedures to reduce fractures, surgery or the like.

Conventional splints may be constructed from uncured plaster-impregnated fabric, or fiberglass impregnated with resin that is water activated. They are initially pliable and soaked in water to activate the curing process. Such conventional splints typically come in rolls or pre sized blanks.

While conventional splints are sufficient for their intended purpose, they do exhibit a number of drawbacks which can be improved upon. For example, some sort of padding must be applied to the limb prior to applying the splint. The splint material must be soaked in water to begin the curing process, and variables such as water temperature and room humidity can alter the cure time for the splint material. Once wetted, the splint material is applied over the padding, which must be kept in proper alignment to be effective. Prior to wetting, the splint material is trimmed to a rough desired shape, but upon wetting and application to a patient, additional trimming of the material is often needed. The process is quite messy, and must be carried out very quickly before the splint material begins to cure. Initial curing can start in 2-5 minutes depending on the product and water temperature used. Once initiated, there is no stopping it and the application process must be completed with precise timing to allow for the body part to be aligned, reduced in fracture or otherwise completed before the splint cures. This process requires considerable training and the practitioner must have the splint in place in time to make the final alignment while the splint is still soft enough. Often, there is a minor complication or the splint is wetted too early or too warm and the curing starts during application so there is not enough time to finish the job properly before curing. In this case, the splint must be discarded and the process started over. This not uncommon occurrence is very wasteful, time consuming and costly, not to mention uncomfortable for the injured patient. Wrapping the padding and splint material can often take two people to support and wrap, and the manipulation is often painful to the patient.

On occasion, for a complicated reduction or alignment of a fracture or other injury, an X-Ray or fluoroscope view is needed during the procedure to see through the body to accomplish the correct procedure. Fiberglass and plaster materials tend to scatter X-rays and are somewhat impenetrable, so the view is typically obscured. These poor images can pose problems and the images must often be made with the patient at odd angles so as to image through the body without imaging through much of the splint. This can require complicated alignment of the machinery and patient which can cause great discomfort and complication.

Additionally, complicated reduction and alignment procedures may require a short period of sedation of the patient as the pain is too great to endure. The patient could react and possibly spoil the procedure. All of this can require a number of qualified people in close proximity doing several procedures at once. Along with the usual practitioners, the group can grow quite large. Everything must be orchestrated precisely and timed with the curing of the splint.

Another concern with conventional splinting materials and techniques is the wet environment created during their use. Because plaster and fiberglass splints will typically remain damp for 12 hours or more as the moisture slowly dissipates from the splint and padding through the Ace®-type wrap, the moist environment from the splint combined with the body's heat and moisture provides the ideal place for bacterial reproduction.

This wet insulated environment also can provide a great deal of discomfort to the patient, especially in warm climates. Additionally, both fiberglass and plaster are virtually sealed against moisture passing through them so the splints do not breath or allow moisture to easily escape from inside near the body. Any moisture management must be provided by the thick padding or other wrapping.

In view of the drawbacks of conventional splints, a need exists for an improved splint which is less messy, requires fewer personnel to apply, has less likelihood of wasted material due to improper application, and is more comfortable and hygienic for the patient.

One proposed improvement on conventional splints is described in commonly assigned U.S. Published Patent Application No. 2012/0101417 to Joseph, which describes a splint having a composite laminate construction, consisting of thermoformable middle layer, and outer layers of foam and/or fabric which represents an improvement on conventional splints. Opportunities for improvement on the splints described therein still exist, however.

Additionally, prior splint constructions utilizing one or more polymer layers for rigidity typically include either a thin layer of polymer sheet material which is prone to flexing and twisting, or a thicker layer which can provide sufficient rigidity but is unable to be formed into complex shapes or contours and is unacceptably heavy.

A need exists, therefore, for an improved construction for splints which is lightweight, formable to the contours of a patient's anatomy, and which is sufficiently rigid to support the injury.

SUMMARY OF THE INVENTION

In one embodiment, the present invention comprises a composite material including a first layer of thermoformable material, a second layer of thermoformable material, and a foam layer disposed between, and bonded to, the first and second layers of thermoformable material, wherein the first and second layers of thermoformable material are heat formable within a target temperature range and substantially rigid at temperatures below a minimum formable temperature of about 130 degrees Fahrenheit.

In another embodiment, the present invention comprises a method including causing a composite material to be manufactured and made available to a user, and providing instructions to the user for creating a splint with the composite material. The composite material comprises a first layer of thermoformable material, a second layer of thermoformable material, and a foam layer disposed between, and bonded to, the first and second layers of thermoformable material, wherein the first and second layers of thermoformable material are heat formable within a target temperature range and substantially rigid at temperatures below a minimum formable temperature of about 130 degrees Fahrenheit. The instructions for creating a splint with the composite material include heating the composite material such that the layers of thermoformable material are above the minimum formable temperature, forming the composite material about a body part while the layers of thermoformable material are above the minimum formable temperature, and holding the composite material in place until expiration of the dwell time such that the layers of thermoformable material are below the minimum formable temperature.

In another embodiment, the present invention comprises a method of applying a splint to a patient, comprising providing a composite material including a first layer of thermoformable material, a second layer of thermoformable material, and a foam layer disposed between, and bonded to, the first and second layers of thermoformable material, wherein the first and second layers of thermoformable material are heat formable within a target temperature range and substantially rigid at temperatures below a minimum formable temperature of about 130 degrees Fahrenheit. The method further comprises heating the composite material such that the layers of thermoformable material are above the minimum formable temperature, forming the composite material about a body part while the layers of thermoformable material are above the minimum formable temperature, and holding the composite material in place until expiration of the dwell time such that the layers of thermoformable material are below the minimum formable temperature.

BRIEF DESCRIPTION OF THE DRAWINGS

Embodiments of the present invention may be more completely understood in consideration of the following detailed description of various embodiments of the invention in connection with the accompanying drawings, in which:

FIG. 3 is a table depicting suitable material properties of a foam layer of the composite material according to an embodiment of the present invention.

Figures 1, 2:
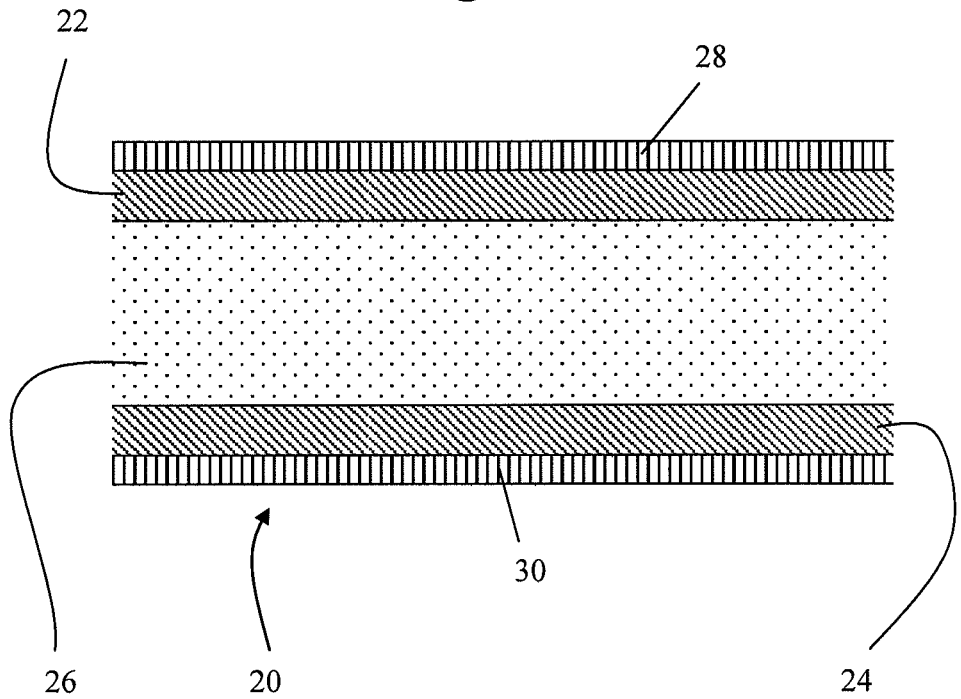
FIG. 1 is a schematic cross-section of the composite material according to an embodiment of the present invention.
FIG. 2 is a table depicting suitable material properties of a thermoformable material layer of the composite material according to an embodiment of the present invention.

While the various embodiments of the invention are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the inventions as may be claimed.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the inventions as claimed.

Although embodiments of the present invention are described chiefly in context of a splint, it should be appreciated that the materials, construction techniques, and methods described herein are also applicable to other orthopedic products such as braces, or for use as supports in combination with other orthopedic products.

The splints described in U.S. Pat. No. 8,303,527 to Joseph and U.S. Published Patent Application No. 2012/0101417 to Joseph, the disclosures of which are incorporated herein by reference, present a significant improvement over conventional wet lay-up splints but room for further improvement still exists. For example, certain splinting situations may call for a more rigid structure than is possible with the materials and structures described in these publications.

Referring now to FIG. 1, embodiments of the present invention generally comprise a composite sandwich material 20, having two layers of thermoformable material 22, 24, separated by a foam core layer 26, and optionally one or more finishing layers 28, 30.

The thermoformable material 22, 24 may include material properties as depicted in FIG. 2. Thermoformable material 22, 24 is preferably rigid at room temperatures, and more preferably rigid at temperatures below about 130 degrees Fahrenheit. Thermoformable material 22, 24 may be heat formable within a target temperature range of about 160-240 degrees Fahrenheit, and more suitably within a range of 190-225 degrees Fahrenheit. The minimum heat formable temperature may be about 160 degrees Fahrenheit, or about 150 degrees Fahrenheit, or about 140 degrees Fahrenheit. Advantageously, the target temperature range is relatively low, allowing quicker heating times, while the minimum heat formable temperature is high enough to prevent unintended alterations of shape during normal use if accidentally exposed to high temperatures.

Within the target temperature range, thermoformable material 22, 24 is pliable and shapeable to the profile of a patient. Thermoformable material 22, 24 may include a dwell time of about three minutes to ten minutes, or of about five minutes to ten minutes. Dwell time refers to the amount of time that thermoformable material 22, 24, once heated to within its target temperature range, is at least partially shapeable. In one embodiment, after being heated to within the target temperature range, thermoformable material 22, 24 is at least partially rigid after five minutes such that during a fitting process, a healthcare professional may cease applying pressure to the splint after five minutes and allow thermoformable material 22, 24 to fully cure without further intervention for the remainder of the dwell time. As utilized in composite material 20, a suitable thickness range of thermoformable layers 22, 24 is from about 0.030 inch to about 0.075 inch for each layer, with a more suitable range from about 0.035 inch to about 0.045 inch for each layer. In another embodiment, the thermoformable material may include glass strand added to the polymer to further increase modulus.

Foam layer 26 preferably comprises a closed cell foam, and is of a relatively high density. Suitable materials for construction of foam layer 26 in whole or in part may include low density polyethylene (LDPE), medium density polyethylene (MDPE), high density polyethylene (HDPE), polyethylene terephtalate glycol-modified (PETG), polyolefin blends, optionally any of these blended with ethylene-vinyl acetate (EVA), and any of which may or may not be crosslinked. One preferred density of foam layer 26 is from about 150 to 300 kg/m^2 or about 16 to 20 lbs/sq. ft. Suitable thickness of foam layer 26 is from about 1 mm to about 3 mm, with a more suitable range from about 1.5 mm to about 2 mm. In one embodiment, the thickness of foam layer 26 is about double the thickness of one layer of thermoformable material 22, 24. In one embodiment, the foam layer has properties as listed in FIG. 3, and is available under the name Microzote which is a LDPE fine celled closed cell foam blown with an inert gas and lacking reactive agents as are commonly used. Foam layer 26 thus provides a connective layer between thermoformable layers 22, 24 that is somewhat compliant and formable when heated, yet rigid and connected enough to resist compression and shearing thus allowing multi-layered composite material 20 to act as a unitized structure.

The combination of two layers of thermoformable material 22, 24 and foam core 26 results in a very light, thin, and rigid piece of composite material 20 which is extremely rigid when formed into a three dimensional shape.

Finishing layers 28, 30 may be selected from a variety of materials. Typically, one of layers 28, 30 will be positioned against the skin of the patient thereby comprising an inner layer, and therefore suitable materials will be comfortable, breathable, antimicrobial, and/or padded, and may comprise closed cell foam, open cell foam, an insulating fabric, a multilayer or lofted insulating fabric layer, or any other suitable material. While open cell foam is desirable for breathability, a closed cell may be advantageous for waterproof characteristics. Optionally, an additional layer may be included which is configured to be in contact with the skin of the patient, the additional layer comprising a fabric that is comfortable on the skin and wicks moisture into the layer 28, 30 for dissipation.

The other of layers 28, 30 will typically comprise an outer layer, and suitable materials will be durable, such as knit nylon spandex blend, knit polyester spandex blend, nylon fabrics, polyester or other fibers that stretch due to the design of the knit, rubberized materials, or foams such as urethane foam, foam rubber or EVA foam. Additionally, unbroken loop fabric, which is operably coupleable to hook-type fasteners, may be included as part of one of layers 28, 30 so as to provide functionality for hook-and-loop (VELCRO®) type fastening arrangements.

Referring now to construction of an embodiment of composite material 20, the multiple layers may be bonded together by means of hot melt, PSA adhesive, or even by heat and pressure alone. In one embodiment, layers 22, 24, 26, 28 and 30 are laminated together at a temperature of 250-300 degrees Fahrenheit, under pressure. Variations on the construction of composite material 20 described herein may be made in order to alter the characteristics of composite material 20. For example, the thickness of the layers of thermoformable material 22, 24 may be varied such that each layer has a unique thickness. The hardness of foam layer 26 may be increased, to increase rigidity. The thickness of foam layer 26 may be varied to vary the dwell time of thermoformable layers 22, 24.

Additional layers of material may also be added as desired, such as spacer fabric, reinforcing material, waterproofing material, and/or additional foam layers for padding. The outer, middle and inner layers may be joined at their edges, such as by sewing, gluing, thermal or chemical bonding, or other suitable methods. Composite material 20 may be perforated with ventilation holes to aid in evaporation and cooling so transport occurs along foam layer 26 and out the vents.

In one embodiment, composite material 20 is provided for splinting, which can be fitted to a patient as follows. Composite material 20 is heated, preferably with a dry heat source such as an oven, microwave, heat gun, radiant lamp heat sources, infrared heaters, a heating bag, pouch, or other heat enclosure, or an exothermic heat source. Wet heat may also be utilized by immersing composite material 20 into a container of hot liquid such as water, or by placing composite material 20 within a liquid-filled bag and placing the bag in a microwave. Composite material 20 is heated for a length of time sufficient to bring the temperature of the layers of thermoformable material 22, 24 within their target temperature range such that composite material is pliable and formable to the patient. In one embodiment, composite material 20 is constructed such that the layers of thermoformable material 22, 24 are within their target temperature range after ten minutes of heating. In another embodiment, composite material 20 is constructed such that the layers of thermoformable material 22, 24 are within their target temperature range after about five minutes of heating.

Once thermoformable material 22, 24 is within its target temperature range, composite material 20 is removed from the heat source and applied to the desired location on the patient. While working in the dwell time of the material, the material is shapeable as desired to the patient, yet will somewhat hold its shape. During heating of the composite material, the thin layers of thermoformable material tend to warm comparatively faster than the foam and fabric layers, reducing the amount of time necessary to heat composite material 20 to its target temperature. Foam layer 26, having a lower density than the thermoformable layers 22, 24, does not retain as much heat as the thermoformable layers 22, 24 so heat dissipates more quickly from thermoformable layers 22, 24 and composite material 20 hardens more rapidly.

An outer bandage wrap may be utilized to retain the material in a desired shape, and/or the physician may hold the material in place with his/her hands while the material cools. In another embodiment, a universal closure system may be provided, such as those described in U.S. Pat. No. 8,303,527 to Joseph and U.S. Published Patent Application No. 2012/0101417 to Joseph. A suitable closure system includes a plurality of attachment members configured to releasably couple to composite material 20 such as by hook-and-loop fasteners, an elongated flexible member configured to be routed through one or more guide elements affixed to the attachment members, and a tensioning mechanism configured to be operable so as to engage the flexible member and tighten the fit of composite material 20.

In another embodiment, the present invention comprises a kit including composite material 20 according to one or more of the embodiments described herein, and a set of instructions recorded on a tangible medium for fitting composite material 20 to a patient as a splint according to the methods described herein. In one embodiment, the instructions may comprise instructions for use (IFU) or directions for use, according to the requirements of one or more regulatory bodies and/or government agencies. The instructions may be intended for a patient, or for a health care professional. Alternatively, the kit may include indications which link a user to electronically accessible instructions.

The composite material 20 described herein may be used in conjunction with other orthopedic products, such as those described in U.S. Pat. No. 8,303,527 to Joseph, U.S. Published Patent Application No. 2012/0101417 to Joseph, and application Ser. No. 13/674,613 to Joseph et al., the disclosures of which are incorporated by reference herein. Composite material 20 may be utilized in place of previously-disclosed rigid supports, or may be used selectively as a supplemental support such as to provide additional support and rigidity in select locations on an orthopedic product.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

What is claimed is:

1. A composite material, comprising:
    a first layer of thermoformable material having a thickness of 0.03 to 0.075 inches, the first layer of thermoformable material being heat formable such that it is at least partially shapeable once heated to within a target temperature range;
    a second layer of thermoformable material having a thickness of 0.03 to 0.075 inches, the second layer of thermoformable material being heat formable such that it is at least partially shapeable once heated to within a target temperature range; and
    a foam layer disposed between the first layer of thermoformable material and the second layer of thermoformable material, the foam layer bonded to the first thermoformable layer and second layer of thermoformable material.

2. The composite material of claim 1, wherein the target temperature range is 160-240 degrees Fahrenheit.

3. The composite material of claim 1, wherein a minimum heat formable temperature is 150 degrees Fahrenheit.

4. The composite material of claim 1, wherein a minimum heat formable temperature is 140 degrees Fahrenheit.

5. The composite material of claim 1, wherein the first and second layers of thermoformable material have a dwell time of three to ten minutes.

6. The composite material of claim 1, and wherein the foam layer has a thickness of 0.04 to 0.12 inches.

7. The composite material of claim 1, wherein the target temperature range is 190-225 degrees Fahrenheit.

8. The composite material of claim 1, wherein the first and second layers of thermoformable material have a density which is three to five times greater than a density of the foam layer.

9. The composite material of claim 1, wherein the density of the first and second layers of thermoformable material is 1200 kg/m$^3$ and the density of the foam layer is 300 kg/m$^3$.

10. The composite material of claim 1, wherein the first thermoformable layer comprises glass strand.

11. The composite material of claim 1, wherein the foam layer is double the thickness of one of the first and second layers of thermoformable material.

12. The composite material of claim 1, further comprising a first finishing layer disposed adjacent to the first layer of thermoformable material opposite the foam layer such that the first layer of thermoformable material is between the first finishing layer and the foam layer.

13. The composite material of claim 12, further comprising a second finishing layer disposed adjacent to the second thermoformable layer opposite the foam layer such that the second thermoformable layer is between the second finishing layer and the foam layer.

14. The composite material of claim 1, wherein the first layer of thermoformable material, the foam layer, and the second layer of thermoformable material are laminated together.

15. The composite material of claim 1, wherein the thickness of the first layer of thermoformable material is different than the thickness of the second layer of thermoformable material.

16. The composite material of claim 1, wherein the foam layer has a lower heat density that the first and second layers of thermoformable material.

17. A composite material, comprising:
    a first layer of thermoformable material having a thickness of 0.03 to 0.075 inches, the first layer of thermoformable material being heat formable such that it is at least partially shapeable once heated to within a target temperature range;
    a second layer of thermoformable material being heat formable such that it is at least partially shapeable once heated to within a target temperature range; and
    a foam layer disposed between the first layer of thermoformable material and the second layer of thermoformable material, the foam layer having a lower density that the first layer of thermoformable material and a lower density that the second layer of thermoformable material.

18. The composite material of claim 17, wherein the target temperature range is in the range of 160-240 degrees Fahrenheit, and wherein the first and second layers of thermoformable material have a dwell time of three to ten minutes.

19. The composite material of claim 18, wherein the first and second layers of thermoformable material have a density which is three to five times greater than a density of the foam layer.

20. The composite material of claim 17, and wherein the foam layer has a thickness of 0.04 to 0.12 inches.

* * * * *